United States Patent [19]

Miller et al.

[11] 4,266,032

[45] May 5, 1981

[54] METHOD OF CULTURING MICROCARRIER SUPPORTED CELLS

[75] Inventors: Robert E. Miller, Balwin; Mau-Jung Kuo, Creve Coeur; Charles Lewis, Jr., Hazelwood, all of Mo.

[73] Assignee: Monsanto Company, St. Louis, Mo.

[21] Appl. No.: 65,652

[22] Filed: Aug. 10, 1979

[51] Int. Cl.³ .............................................. C12N 5/02
[52] U.S. Cl. ...................................... 435/241; 435/286
[58] Field of Search ...................... 435/240, 241, 286

[56] References Cited

U.S. PATENT DOCUMENTS

| 3,816,261 | 6/1974 | Torney | 435/253 |
|---|---|---|---|
| 3,887,430 | 6/1975 | Torney et al. | 435/241 |
| 3,953,290 | 4/1976 | Uthne et al. | 435/240 |
| 4,055,466 | 10/1977 | Torney | 435/241 |

*Primary Examiner*—Alvin E. Tanenholtz
*Attorney, Agent, or Firm*—Scott J. Meyer; James W. Williams, Jr.

[57] ABSTRACT

A method of submerged cell culture is provided which employs a microcarrier support comprising cross-linked polystyrene resin beads derivatized with amino acids, peptides, or hydroxy carboxylic acids.

13 Claims, No Drawings

METHOD OF CULTURING MICROCARRIER SUPPORTED CELLS

BACKGROUND OF THE INVENTION

This invention relates to a method for the culture of cells and, more particularly, to the submerged culture of animal cells using microcarriers for the attachment of cells in suspension.

The successful use of microcarriers for cell culture was first reported by van Wezel, Nature 216, 64–65 (1967). The method of van Wezel consisted of growing cells as monolayers on the surface of positively charged DEAE-Sephadex ® beads(grade A-50, about 100$\mu$ diameter) suspended in culture media in a stirred vessel. The stirred vessel used by van Wezel was the Bilthoven microbial culture unit described by van Hemert, Biotechnol. Bioeng. VI, 381–401 (1964). In this method, different cell lines, human diploid cells, and primary rabbit kidney cells were successfully cultivated. The production of polio virus in the microcarrier culture was examined by van Wezel and the virus multiplication was found to be essentially similar to that in monolayer culture.

Other microcarriers or particulate support materials which have been disclosed heretofore as useful for the attachment of cells in suspension culture are the porous Spherosil ® silica spherules (about 125–150$\mu$ diameter) described in U.S. Pat. No. 3,717,551; the collodion (nitrocellulose) coated DEAE-Sephadex beads of van Hemert et al, Biotechnol. Bioeng. XI, 875–85 (1969); the glass beads (3.5–4 mm diameter) taught by Wöhler et al, Exper. Cell. Res. 74, 571–3 (1972) and German Offenlegungsshrift No. 2,300,567; the QAE-Sephadex, CM-Sephadex and Dowex ® 1-X8 beads described by Horng and McLimans, Biotechnol. Bioeng. XVII, 713–32 (1975); the silicone-treated polycarbonate beads mentioned in Netherlands Patent Application No. 76 05,438, Nov. 23, 1976; the polyacrylonitrile particles taught in U.S. Pat. No. 4,024,020; the CMC-coated DEAE-Sephadex beads disclosed in U.S. Pat. No. 4,036,693; and the formal or butyral coated DEAE-Sephadex beads described in German Offenlegungsshrift No. 2,834,067.

In another prior disclosure, U.S. Pat. No. 3,887,430, certain basic anion exchange resins accompanied by a lipid source such as polysorbate 60 are suggested as useful support materials for the growth of cells in tissue culture. The resins used in said combination with a lipid source are described as based on a vinyl aromatic compound such as styrene copolymerized with a cross-linking agent such as divinylbenzene and then reacted with a halomethylating agent such as chloromethyl methyl ether to produce a halomethylated polystyrene. The halomethylated polymeric product is then reacted with a primary or secondary amine or with a polyamine such as polyalkylenepolyamine to produce the basic anion exchange resin. These resins are stated to be useful for tissue culture of animal cells such as primary chick embryo and Madin-Darby bovine kidney cells and for propagating virus such as measles and mumps virus.

Notwithstanding the variety of microcarriers taught in foregoing art, the discovery and development of new types of microcarriers for cell culture is much sought after since the particular requirements for culture of certain cells are not satisfactorily met by the known microcarriers.

BRIEF SUMMARY OF THE INVENTION

In accordance with the present invention a method of submerged cell culture is provided which employs a microcarrier support comprising cross-linked polystyrene resins derivatized with amino acids, peptides, or hydroxy carboxylic acids.

DETAILED DESCRIPTION OF THE INVENTION

The cross-linked polystyrene resins derivatized with amino acids, peptides or hydroxy carboxylic acids can be prepared in a manner somewhat similar to the method for preparing the basic anion exchange resins described in U.S. Pat. No. 3,887,430, except that amino acid, peptide or hydroxy carboxylic acid derivatives are made instead of amine or polyamine derivatives, the amino acids are not alkylated on the amine fuction, and no lipid source need be used in combination with the resin.

In accordance with this procedure, a vinyl aromatic compound such as styrene is copolymerized with a cross-linking agent such as divinylbenzene to produce a cross-linked polystyrene. The latter polymeric substance is then reacted with a halomethylating agent such as chloromethyl methyl ether to produce a halomethylated polystyrene. The halomethylated materials and suitable methods for their preparation are described in further detail in U.S. Pat. Nos. 2,591,574; 2,597,439; and 2,642,417. The disclosure of said patents is incorporated by reference herein.

In order to prepare the amino acid derivatives, according to one method, the aforesaid haloalkylated material is first reacted in the presence of a tertiary amine, such as triethylamine, with an amino acid that has been protected with an N-protective reagent, such as one containing the carbobenzoxy group or the t-butyloxy-carbonyl group (BOC). Following the amino acid derivatization, the N-protective group is removed by a conventional cleaving agent such as HCl or HBr in acetic acid or trifluoroacetic acid in dichloromethane. Peptides can then be formed by similar such addition of the same or different amino acids to the chain. Such amino acid and peptide derivatives and their preparation are described in further detail by Merrifield, J. Amer. Chem. Soc. 85, 2149–54 (1963) and Science 150, 178–85 (1965).

The general reaction for preparing the above amino acid derivatized product can be illustrated as follows:

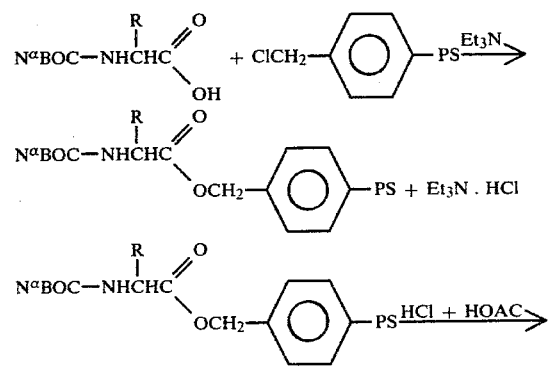

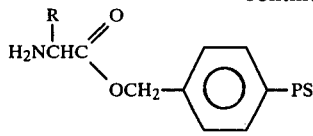

wherein PS = polystyrene The N-terminal amine of the latter product can then be reacted with the activated carboxyl of the next protected amino acid to form the first pepetide bond to form a peptide derivatized product.

In accordance with another method of preparation, cesium bicarbonate is used instead of the tertiary amine in the above procedure to provide a microcarrier which is free from quaternary salt. The latter method is described in detail by Gisen, *Helv. Chim. Acta* 56, 1476 (1973).

The hydroxy carboxylic acid derivatized resins can be prepared in a manner analogous to the method for preparing the amino acid derivatized resin except that it is unnecessary to use the N-protective or blocking reagents with the hydroxy carboxylic acids.

Although amino acid and hydroxy carboxylic acid attachment typically varies between about 0.01 and about 0.67 millimole of amino acid or hydroxy carboxylic acid per gram of derivatized cross-linked polystyrene resin, the preferred range for cell growth has been found to be about 0.2 to about 0.6 millimole per gram.

The size of the derivatized resin beads also can vary widely. As an example, in the case of a preferred glycine-derivatized resin, the beads falling within a size range of 20-64 microns diameter amounted to about 99% of the bead volume and 49-51% of the bead population. The surface area of the bead was 0.1406 square meters per gram (BET method)* and the number of beads per gram was $1.3 \times 10^7$. It should be understood, however, that the invention is not limited to these resin bead values which are given for purposes of illustration and not limitation.

*Brunauer, Emmett and Teller, *J. Amer. Chem. Soc.* 60, 309 (1938).

Representative amino acids which have been covalently reacted in the foregoing manner include the aliphatic amino acids:
  glycine, valine, alanine, serine, cysteine, glutamic acid, lysine and arginine;
  the aromatic amino acid tyrosine;
  and the heterocyclic amino acids:
  proline and tryptophan.

Illustrative peptide derivatives which have been synthesized according to the above procedure include the homopolymer having an attached octaglycine and heteropolymers having the attached peptides:

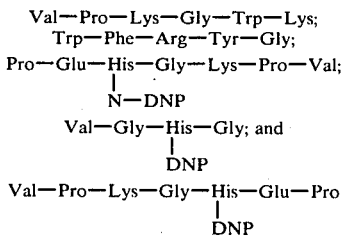

wherein DNP = dinitrophenyl

Exemplary hydroxy carboxylic acids which have been used for derivatization according to the above procedures include gluconic acid, lactobionic acid, and glycolic acid.

The microcarriers thus produced are useful for culturing primary cells, human diploid cells, tumorous cells and established cell lines. It will be appreciated that not all cells and cell lines may be readily adaptable to each of the amino acid, peptide or hydroxy carboxylic acid derivatized beads. Thus, it has been found that while primary rhesus monkey kidney cells attach and grow well on glycine and proline derivatized resins, relatively poorer growth of these cells was observed with phenylalanine, tyrosine and cysteine modified resins. Glycine and proline derivatized resins also have been found to be eminently suitable for culturing primary rat mammary cells, primary calf anterior pituitary cells, and primary human fetal kidney cells. Human peripheral lymphocyte cells which are normally difficult to culture on any of the heretofore known microcarriers have been grown particularly well on the proline derivatized resins. Lysine, serine, gluconic acid, glycolic acid and lactobionic acid derivatized beads also were good for cell growth of primary rhesus monkey kidney cells while foreskin fibroblasts grew well on the glycine and proline derivatized microcarriers. The cell growth and attachment to the amino acid, peptide and hydroxy carboxylic acid derivatized beads of this invention is obtained without need to employ in combination therewith any lipid source material such as the polysorbate 60 required for the amine and polyamine derivatized resins described in U.S. Pat. No. 3,887,430.

The microcarrier supported cell culture can be carried out in agitated liquid suspension media using any of the well-known tissue culture media. Illustrative suitable media are, for example, Basal Medium Eagle's (BME), Eagle's Minimum Essential Medium (MEM), Dulbecco's Modified Eagle Medium, Medium 199 and balanced salt solutions (BSS) such as those of Earle and Hanks fortified with various nutrients. These are commercially available tissue culture media and are described in detail by H. J. Morton, *In Vitro* 6, 89–108 (1970). These culture media contain assimilable sources of nitrogen, carbon and inorganic salts which can be provided by essential amino acids, mineral salts, vitamins and carbohydrates. They are also frequently fortified with mammalian sera such as fetal calf serum.

The following detailed examples will further illustrate the invention although it will be appreciated that the invention is not limited to these specific illustrative examples.

EXAMPLE 1

In order to prepare microcarrier by derivatizing chloromethylated polystyrene beads with amino acid, the following procedure was carried out:

To 397.0 grams of chloromethylated polystyrene beads (Vega Fox #12417, Tucson, Ariz., 2% cross-linked, 3.72% Cl−) suspended in 2500 ml absolute ethanol was added 135 ml of triethylamine and 220.5 grams of Nα-BOC-glycine (Vega Fox #10876-1, 1.26 moles, 0.00317 moles/gram resin). The suspension was stirred at reflux for 108 hours. The solid was recovered by filtration, washed three times with 250 ml absolute ethanol, three times with 250 ml of a solution of ethanol and water in equal parts by volume, and then three times with 250 ml absolute ethanol. The solid was dried under vacuum to give 471.7 grams of product. Analysis indicated 0.547 mM glycine/gram of beads, 1.07% nitrogen, 0.66% total chlorine and 0.23% ionic chlorine. The surface area determined by the BET method was 0.1008 m²/gram.

Other amino acid derivatives were prepared in a manner substantially similar to the procedure of the above example by substituting the corresponding blocked amino acid for an equivalent amount of the blocked glycine used in said example. Likewise, hydroxy carboxylic acid derivatives were analogously prepared by substituting the corresponding unblocked hydroxy carboxylic acid for an equivalent amount of the blocked glycine in the foregoing example.

EXAMPLE 2

In order to prepare microcarrier free from quaternary salts, the following procedure was carried out:

The cesium salt of the derivatized amino acid was prepared by dissolving 1.46 g Nα-BOC-glycine (0.0083M) in 25 ml distilled water followed by the addition of 2.5 g of cesium bicarbonate dissolved in 25 ml distilled water. The resultant solution (pH 7.0) was stirred for one hour at room temperature (ca. 20°-22° C.). After evaporation to dryness, the solid was stored over $P_2O_5$ for 20 hours.

The dried cesium salt was added to a suspension of 7 g. of chloromethylated polystyrene beads in 60 ml of redistilled dimethylformamide. The mixture was stirred at 60°-65° C. for 15 hours. Derivatized resin was recovered by filtration and washed once each with distilled water, DMF: water (9:1 v/v), DMF and finally absolute ethanol. Analysis of the dried product indicated 0.935 mM glycine/g of beads, 1.74% total chlorine and 0.72% ionic chlorine. The surface area determined by the BET method was 0.1176 $m^2/g$. Phenol red dye adsorption was negative, thereby indicating the absence of quaternary salts.

EXAMPLE 3

In order to remove the BOC blocking group from microcarrier and prepare the resin beads for use in cell culture, the following procedure was carried out:

To a given sample of BOC-derivatized amino acid resin microcarrier (prepared as in Examples 1 or 2, above) were added four volumes of methylene chloride to swell the beads. Excess solution was removed by filtration. This wash cycle was repeated two additional times. Swollen resin then was shaken for 30 minutes at room temperature in a solution of 50% trifluoroacetic acid in methylene chloride (4 volumes) to hydrolyze the t-butyl-oxycarbonyl blocking groups from the α-amine of the amino acid. Excess acid was removed by washing the beads three times with methylene chloride followed by three absolute ethanol washes. At this point a second amino acid residue was added (in some instances) as in conventional Merrifield peptide synthesis, or the resin beads were prepared for cell inoculation. In the latter case, the beads were slurried in normal physiologic saline (0.15 Molar NaCl) and the pH adjusted to 7.0 with dilute NaOH. The suspension was filtered and the washing with saline at pH 7.0 was repeated three times. Sufficient beads to give a final concentration of 5 g per liter were suspended in 10-15 ml of normal physiologic saline, transferred to a reaction vessel and autoclaved at 125° C. for 30 minutes.

Since no BOC-blocking groups were used in preparation of the hydroxy carboxylic acid derivatives, the resin beads in such case were directly prepared for cell inoculation without the need to remove any blocking group as required in the case of the blocked amino acid derivatives.

EXAMPLE 4

A 500 ml stirred cell culture reaction vessel was charged with 2.8 grams of amino acid derivatized, cross-linked polystyrene beads suspended in about 10-15 ml of saline. The system was autoclaved and, after cooling, culture medium was added to a volume of 450 ml. The culture medium consisted of synthetic Medium 199 [See Morton, In Vitro 6 (2), 89-108 (1970)] containing 10% fetal bovine serum. A 50 ml aliquot of a suspension of $1 \times 10^6$ primary rhesus monkey kidney cells per ml was added to the reactor and the system was stirred for one to two minutes. The contents of the vessel were allowed to settle overnight (about 15 hours) in a 5% $CO_2$-air incubator maintained at 38° C. The suspension was agitated and a 50 ml aliquot was removed for the day 1 DNA analysis.

For the remainder of the cell culture period, the system was stirred at about 100 to 150 rpm. At each of days 6, 9, 14 and 21 a 25 ml aliquot was removed for DNA analysis. Medium was replaced with fresh medium in the vessel at days 6, 9 and 14.

A series of 16 amino acid derivatized, cross-linked polystyrene beads, prepared as in Examples 1 and 3 with the appropriate amino acids, was evaluated in the foregoing manner. The following Table I shows the degree of amino acid attachment in millimoles of amino acid per gram of resin and the ratio of DNA per gram of resin in the day 14 aliquot vs. the day 1 aliquot for each amino acid derivatized microcarrier support. DNA content of the cells was selected as the parameter of relative cell growth, and growth of cells after 14 days was taken as representative of full growth.

TABLE I

| Amino Acid | mM/g of amino acid | Ratio of DNA/gm of bead for day 14 aliquot vs. day 1 aliquot |
|---|---|---|
| Glycine | 0.114 | 10 |
| Glycine | 0.172 | 10 |
| Glycine | 0.547 | 11 |
| Proline | 0.087 | 8 |
| Proline | 0.402 | 11 |
| Proline | 0.486 | 13 |
| Proline | 0.423 | 14 |
| Serine | 0.339 | 12 |
| Glutamine | 0.199 | 8 |
| Valine | 0.144 | 8 |
| Lysine | * | 9 |
| Alanine | 0.190 | 7 |
| Tryptophan | 0.517 | 4 |
| Cysteine | 0.153 | 3 |
| Tyrosine | 0.379 | 4 |
| Pyroglutamic acid | 0.378 | 2 |

*not analyzed

In the case of the foregoing glycine- and proline-derivatized resins, the attachment and spreading of monkey kidney cells on the surfaces was also confirmed by election photomicrography.

EXAMPLE 5

The cell culture procedure of Example 4 was essentially repeated with the following two peptide derivatives of cross-linked polystyrene instead of the amino acid derivatives as the microcarrier:

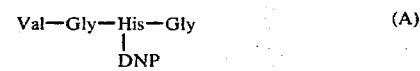

-continued $$\underset{\mathrm{DNP}}{\mathrm{Val-Pro-Lys-Gly-His-Glu-Pro}} \quad \text{(B)}$$

Cell attachment and growth was observed but the growth rate was slower than that observed for glycine, valine, proline, and alanine derivatized cross-linked polystyrene beads prepared as in Examples 1 and 3. The ratio of DNA/gm of bead for day 14 aliquot vs. day 1 aliquot was 3.7 for peptide (A) and 0.4 for peptide (B).

EXAMPLE 6

The cell culture procedure for Example 4 was essentially repeated with the following three hydroxy carboxylic acid derivatives of cross-linked polystyrene instead of the amino acid derivative as the microcarrier:
(A) Gluconic acid
(B) Lactobionic acid
(C) Glycolic acid Excellent cell attachment and growth was observed in which the ratio of DNA/gm of bead for day 14 aliquot vs. day 1 aliquot was as follows:
(A) 14.0
(B) 10.0
(C) 9.00

EXAMPLE 7

Primary human fetal kidney cells were cultured for 23 days in substantially the same manner as in Example 4 on glycine derivatized, cross-linked polystyrene beads (0.172 mM/gm) and on proline derivatized, cross-linked polstyrene beads (0.486 mM/gm). From an inoculum of $45 \times 10^6$ cells in a 500 ml reactor, the day 1 aliquots showed 230 μg DNA per gram of resin (about $23 \times 10^6$ cells per gram). At day 13, the glycine-derivatized resin indicated a 3-fold increase in DNA and the proline-derivatized resin showed a 5-fold increase in cell density. At termination of the runs (23 day culture) the DNA per gram for the glycine-derivatized resin was 1559 μg ($6.8 \times$ day 1; $1.6 \times 10^8$ cells/gm); the DNA for the proline-derivatized resin was 1782 μg ($7.7 \times$ day 1; about $1.8 \times 10^8$ cells/gm).

EXAMPLE 8

Human peripheral lymphocytes were isolated from blood by leukophoresis sedimentation on a layer of Ficoll-Paque ® (Pharmacia Fine Chemicals AB). Ficoll-Paque is an aqueous solution containing 5.7 grams of a synthetic high molecular weight ($\overline{M}_w$ 400,000) polymer of sucrose and epichlorohydrin in 9 grams of diatrizoate sodium in every 100 ml. The separated cells were then cultured in RPMI-1640 medium supplemented with 10% fetal bovine serum and containing a suspension of 5 grams/liter of proline-derivatized, cross-linked polystyrene resin beads (0.486 mM/gram), according to the procedure described by Eitoh, *J. Nat. Cancer Inst.* 52, 1403-7 (1974). Strong growth and attachment of cells to the microcarrier was obtained; whereas, by comparison no significant growth or attachment was obtained in a similar run using DEAE-Sephadex (A-50) beads as a control instead of the proline-derivatized resin.

EXAMPLE 9

Primary calf anterior pituitary cells were grown in suspension culture according to the procedure described by Horng and McLimans, *Biotechnol. Bioeng.* XVII, 713-32 (1975). In two runs, proline-derivatized, cross-linked polystyrene beads were used as the microcarrier; in a third run glycine-derivatized, cross-linked polystyrene beads were used; while in a fourth run DEAE-Sephadex beads were used as a control for comparison. On a rating scale of 0-12 (maximum cell growth is 12), the two proline-derivatized resins gave scores of 6 and 11, the glycine-derivatized resin gave a score of 9, and the DEAE-Sephadex control gave a score of 8.

EXAMPLE 10

Primary rat mammary cells were grown in suspension culture according to the procedure of Example 9. The growth results produced a score (on the same rating basis as Example 9) of 11 for the glycine-derivatized resin; scores of 10 and 12 for the two proline-derivatized resins; and a score of 12 for the DEAE-Sephadex control resin.

EXAMPLE 11

A 500 ml stirred cell culture reactor charged with 3.2 grams of a glycine derivatized resin (prepared as in Examples 1 and 3) and 500 ml of medium 199 containing 10% fetal bovine serum was inoculated with 75 ml of $1 \times 10^6$ primary rhesus monkey kidney cells. After 15 days of cell culture at 37° C. the cell number had increased to $55.6 \times 10^4$ cells/ml vs. the $4.78 \times 10^4$ cells/ml on day one.

EXAMPLE 12

A 500 ml stirred cell culture reactor was charged with 2.39 grams of a glycine derivatized resin (prepared as in Examples 1 and 3) and 500 ml of medium 199 containing 10% fetal bovine serum. The vessel was inoculated with 50 ml of $1 \times 10^6$ primary human fetal kidney cells (Gibco). The cell number on day one was $11.2 \times 10^4$ cells/ml and after 23 days of cell culture at 37° C. the cell number had increased to $74.8 \times 10^4$ cells/ml., about a sevenfold increase.

EXAMPLE 13

In order to demonstrate the growth of cells on microcarrier free from quaternary salt, human diploid foreskin fibroblast cells were grown on cross-linked polystyrene resin derivatized with proline in the presence of cesium bicarbonate (Proline-$CsHCO_3$ derivative) in a manner analogous to the procedure of Examples 2 and 3 using $N\alpha$-BOC-proline instead of $N\alpha$-BOC-glycine. The cells were cultured in Medium 199 supplemented with 10% fetal bovine serum and charged with the microcarrier as in Example 4. At each of days 1,5,8, 12, 15 and 19, aliquots were removed and analyzed for DNA content. For purposes of comparison, a similar cell culture run was made in which the microcarrier was a cross-linked polystyrene resin derivatized with glycine in the presence of triethylamine (Glycine-$Et_3N$ derivative) in accordance with the procedure of Example 1. The following Table II shows the micrograms of DNA per gram of resin for both of the foregoing runs.

TABLE II

| | μg DNA/gm Resin | |
|---|---|---|
| Day | Proline ($CsHCO_3$) Derivative | Glycine ($Et_3N$) Derivative |
| 1 | 28.4 | 13.4 |
| 5 | 73.7 | 39.1 |

TABLE II-continued

| | μg DNA/gm Resin | |
|---|---|---|
| Day | Proline (CsHCO$_3$) Derivative | Glycine (Et$_3$N) Derivative |
| 8 | 82.8 | 52.7 |
| 12 | 62.4 | 78.1 |
| 15 | 71.4 | 74.2 |
| 19 | 101.4 | 93.6 |

Various other examples can be devised by the person skilled in the art to which the invention pertains after reading the present disclosure without departing from the spirit and scope of the invention. All such further examples are included within the scope of the appended claims.

What is claimed is:

1. In the method of growing anchorage dependent cells in suspension the improvement comprising employing in the suspension as a microcarrier support for attachment of cells a cross-linked polystyrene resin derivatized by reaction with material selected from the group consisting of amino acid, peptide and hydroxy carboxylic acid and bonded thereto through a carboxyl group of said material.

2. The method of claim 1 in which the resin is derivatized with an amino acid.

3. The method of claim 2 in which the amino acid is glycine.

4. The method of claim 2 in which the amino acid is proline.

5. The method of claim 4 in which the cells are human peripheral lymphocyte cells.

6. The method of claim 1 in which the cells are primary monkey kidney cells.

7. The method of claim 6 in which the amino acid is lysine.

8. The method of claim 6 in which the amino acid is serine.

9. The method of claim 2 in which the amount of amino acid in the microcarrier ranges from about 0.2 to about 0.6 millimoles per gram of microcarrier.

10. The method of claim 1 in which the resin is derivatized with a hydroxy carboxylic acid.

11. The method of claim 10 in which the hydroxy carboxylic acid is gluconic acid.

12. The method of claim 10 in which the hydroxy carboxylic acid is lactobionic acid.

13. The method of claim 10 in which the hydroxy carboxylic acid is glycolic acid.

* * * * *